(12) United States Patent
Eimer et al.

(10) Patent No.: US 6,277,311 B1
(45) Date of Patent: Aug. 21, 2001

(54) METHOD OF FORMING FLOWABLE UREA HAVING LOW BIURET CONTENT

(75) Inventors: Kenneth E. Eimer, Rainier; Harold G. Nelson; Sante P. Valpiani, both of St. Helens, all of OR (US); Douglas E. Chandler, Cheyenne, WY (US); Mark C. Anderson, Spring, TX (US)

(73) Assignee: Costal States Management Corporation, Houston, TX (US)

( * ) Notice: Subject to any disclaimer, the term of this patent is extended or adjusted under 35 U.S.C. 154(b) by 0 days.

(21) Appl. No.: 09/371,560

(22) Filed: Aug. 10, 1999

(51) Int. Cl.[7] .............................. B29B 9/02; B29B 9/08; B29B 9/12
(52) U.S. Cl. ............................................ 264/117; 264/118
(58) Field of Search ....................................... 264/117, 118

(56) References Cited

U.S. PATENT DOCUMENTS

| | | |
|---|---|---|
| 3,689,607 | 9/1972 | Backlund . |
| 3,819,310 | 6/1974 | Mavrovic . |
| 3,903,158 | 9/1975 | Fuentes et al. . |
| 3,933,956 | 1/1976 | Mavrovic . |
| 3,936,499 | 2/1976 | Zardi et al. . |
| 4,069,253 | 1/1978 | Kanai et al. . |
| 4,190,622 | 2/1980 | Landis . |
| 4,390,483 | 6/1983 | Willems et al. . |
| 4,525,198 | 6/1985 | Van Hijfte et al. . |
| 4,654,442 | 3/1987 | Young et al. . |
| 4,997,469 | 3/1991 | Moore . |

OTHER PUBLICATIONS

Brochure: "CPM—Series 3000 Pellet Mills," CPM, Crawfordsville, IN, 1989.
Brochure: "CPM—The World's Largest Designer and Manufacturer of Pellet Mills and Pelleting Equipment." CPM, Crawfordville, IN, 1993.
Brochure: "CPM Pelleting Systems—Putting Your Future in Perfect Shape." CPM, Crawfordville, IN, 1995.
Brochure: "Kahl Process Technology: Pelleting—the Economic Way of Compacting and Shaping." Kahl LCI Corporation, Charlotte, NC. Admitted prior art (Undated).
Brochure: "Briquetting with Roller Presses," Koppern Equipment, Inc., Charlotte, NC, 1995. Admitted prior art.
R. Zisselmar and N. Klinker: "Compaction/Granulation of Fertilisers." Publication No. 10.2, Koppern, Hattingen/Ruhr, Fed. Rep. of Germany. Admitted prior art, (Undated).
Brochure: "Compaction with Roller Presses." Koppern Equipment, Inc., Pittsburgh, PA, 1994.
W. Pietsch, "Granulation of Fertilizers by Compaction." Publication No. 11.0, Koppern Equipment, Inc., United States, 1989.
Flier: "Low Pressure to High Pressure . . . A Variety of Pelleting Solutions!" LCI Corporation, Charlotte, NC. Admitted prior art, (Undated).

*Primary Examiner*—Leo B. Tentoni
(74) *Attorney, Agent, or Firm*—Jennifer S. Sickler; Michael Coblenz; Gardere Wynne Sewell

(57) ABSTRACT

A method for producing urea having a low biuret content comprising providing solid crystals of urea and forming the solid crystals into discrete masses of urea by mechanical compacting.

14 Claims, No Drawings

METHOD OF FORMING FLOWABLE UREA HAVING LOW BIURET CONTENT

BACKGROUND OF THE INVENTION

1. Field of the Invention

The present invention relates to urea having a low biuret content and, more particularly, to a method of converting crystalline urea into a physical form that has desirable flow properties, resistance to caking and dust formation without any attendant increase in the concentration of biuret.

2. Description of the Prior Art

Urea finds use in a variety of applications. For example, urea is widely used as an agricultural fertilizer. When used as a fertilizer, urea can simply be broadcast on the ground or dissolved in a solution that is sprayed on the foliage of growing plants. In the former case, biuret content is relatively unimportant. However, when used as a foliage spray, the biuret content becomes critical. It is well known that biuret, formed by the condensation of two molecules of urea with the loss of one molecule of ammonia, is noxious to plant life since it exhibits a very active phytotoxic action. Accordingly, to produce a foliar grade urea, it is generally necessary that the urea have a maximum biuret content of 0.25% by weight, more preferably 0.15% by weight or less.

In addition to its use for agricultural purposes, urea has numerous other applications wherein it is required that the biuret content be low. For example, low biuret ureas are necessary in the production of certain synthetic resins and plastics, in pharmaceutical products, in solutions for textile treating and finishing, etc.

High purity crystals of urea can be produced by a process of reacting ammonia and carbon dioxide at high pressures and temperatures to form ammonium carbamate, which, under the reaction conditions, is converted into urea and water. The resulting mother liquor containing urea, ammonium carbamate, ammonia, and water is then treated by various processes to obtain solid urea crystals.

Although urea crystals of high purity and low biuret content can be produced, they are not satisfactory for normal handling, storage, or shipment due to their tendency to agglomerate. Accordingly, most of the industrial and agricultural grades of urea are in the form of prills made in prilling towers or the like well known to those skilled in the art. An inherent problem with the prilling of urea is that the urea is usually heated to or near its melting point with a consequent increase in the biuret content.

SUMMARY OF THE INVENTION

It is therefore an object of the present invention to provide a method for converting crystalline urea into a physical form that is commercially acceptable in terms of flow properties and has a low biuret content.

Another object of the present invention is to provide a method for converting crystalline urea into a form that is low in biuret content and resistant to caking and dust formation.

Still another object of the present invention is to provide a method for producing urea having a low biuret content that is free-flowing and has ready solubility in water.

The above and other objects of the present invention will become apparent from the description given herein and the appended claims.

In accordance with the present invention, there is provided a method for producing urea having a low biuret content comprising providing solid crystals of urea and forming said solid crystals into discrete, cohesive masses by the use of mechanical compacting techniques. One advantage of the present invention is that melting of the urea crystals is avoided, thereby virtually eliminating any increase in biuret content over and above that which is initially present in the solid crystals.

DESCRIPTION OF THE PREFERRED EMBODIMENTS

The present invention is based on the surprising finding that urea crystals can be formed by mechanical compacting techniques into larger discrete masses that exhibit good flow properties and resistance to caking and dust formation while still maintaining acceptable solubility in water and other aqueous media without increasing the biuret content of the urea.

The production of urea crystals having low biuret content, e.g., less than 0.15% by weight, is well known by those skilled in the art. Typically, in the process the crystalline urea is recovered from a mother liquor that, in addition to the urea, contains biuret and small amounts of ammonia and water. To separate the urea crystals from the mother liquor, it is common, as well known to those skilled in the art, to evaporate the mother liquor using subambient pressure and then separate the solid urea crystals by techniques such as centrifugation, filtration, decantation, or other techniques commonly used to separate solids from solutions. To remove impurities such as biuret from the solid urea crystals, it is also common to wash the crystals with small amounts of water.

Once the solid urea crystals have been washed, they can be dried, as, for example, using heated air, at a temperature of from 55–95° C. Solid urea crystals produced in this fashion typically have a biuret content of less than 0.2%, commonly less than 0.15% by weight. Generally, urea crystals have a biuret content of from 0.07–0.12% by weight. Accordingly, the biuret content of the urea crystals produced according to the process described above are eminently suited, at least as to biuret content, for agricultural, pharmaceutical, industrial, and virtually any other usage to which urea is put. However, as noted above, urea crystals cannot be easily handled, stored, or shipped due to their tendency to pack or agglomerate, and, accordingly, it becomes economically and commercially necessary to form the solid urea crystals into prills, which, as noted above, raises the biuret content to a level that for many applications makes the urea undesirable for use at best and totally unusable at worst.

To solve the above problems, the present invention contemplates compacting of the solid urea crystals by virtually any mechanical technique in which the solid crystals of urea are formed into larger masses without the use of heat, other than as may be generated in the mechanical compacting technique and, in any event, at a temperature substantially below the melting point of urea. The size enlargement—i.e., the formation of the solid urea crystals into larger, discrete masses—can be accomplished by techniques such as nodulizing, pelletizing, tableting, briquetting, roll pressing, etc. Of these various mechanical compacting techniques, pelletizing is preferred.

In the case of nodulizing, the solid urea crystals can be gathered into larger discrete masses of more or less spherical form by working them together, as, for example, in a ball mill or similar apparatus. However, this form of compacting is less preferred due to the tendency for heat buildup to occur during the working of the solid urea crystals. Moreover, there is a tendency of the end product to have low crush strength and be less flowable.

The more preferred methods of mechanical compacting involve the use of pressure, with or without shear and mixing, such as occurs in extrusion/pelletizing.

In the case of tableting, tableting presses of the rotary type can be employed.

Another type of mechanical compacting that can be employed is roll pressing, which utilizes the principle of press-agglomeration. In this process, the solid urea crystals are introduced into the nip of two counter-rotating rollers by means of a suitable feed—i.e., a screw. As the solid urea crystals are compacted, the pressure in the compacted masses increases. The product is typically a flat sheet of 5–20 mm thickness. The sheet produced by the roller press method can then be broken up into smaller pieces and classified into the desired particle size range.

Briquetting, another technique for forming the discrete masses of solid urea crystals, is a variation of the roll pressing technique wherein the solid urea crystals are fed into the space between and above counter-rotating rolls that have peripheral cavities. As the rolls separate, the briquets are discharged. Typically, the briquets are soft in their centers and hard on the surfaces and edges, where there are greater pressure and particle rearrangements. Suitable roller presses and briquetting presses are marketed by Koppern Equipment, Inc. and K. R. Komarak Briquetting Research, Inc., to mention a few.

As noted above, the preferred mechanical compacting technique is pelletizing, which can be accomplished in pellet mills or other similar pelletizing equipment. Pelletizing is associated with the application of force in a manner that includes rubbing, shearing, and mixing—i.e., it involves extrusion. Extrusion devices that can be used for size enlargement or pelletizing include presses that may be hydraulic or mechanical in their operation or of the roller and die type wherein a roller or a set of rollers operating within a perforated die ring forces the solid urea crystals into holes and compacts them such that a continuous solid rod exits from the hole, which typically breaks off into small cylindrical sections or, if necessary, can be cut off by a knife at the periphery of the hole. Suitable pellet mills are available from CPM (California Pellet Mill Co.).

As can be seen from the above, virtually any type of mechanical compacting can be employed, the only requisite being that the particular technique not generate any significant amounts of heat such that the biuret content increases. While it will be recognized that virtually any mechanical compacting technique induces some heating, such heating is far below that necessary to melt the urea and, accordingly, far less than that necessary to induce the formation of biuret.

Compacted urea masses prepared by the preferred methods noted above exhibit high crush strength and good anti-caking properties, and are flowable. It is apparent that the size of the compacted masses of urea produced according to the method of the present invention can vary widely depending upon the type of mechanical compacting employed. For example, briquettes can be made in sizes wherein the thickness ranges from 9–50 mm, the height ranges from 16–70 mm, and the width varies from 19–100 mm. Roll compacted product, which has been crushed and screened, can range in size from 4–200 mesh. Tablets can range in size from ¼" to ½" and larger, while pellets can range from ¼ to ½" in diameter, with lengths of virtually any size, e.g., from ⅛" to 1" or larger. However the discrete masses are formed, it is preferred that they be sized such that they retain good flow characteristics and good crush strength consistent with being small enough to exhibit adequate solubility. Although the compacted masses of urea produced by the method of the present invention have good solubility in water and other aqueous solutions, their dissolution rate tends to be lower than that of typical urea prills. This relatively lower dissolution rate can be readily overcome by various particle reduction techniques, such as crushing or grinding. For example, typical size reduction equipment that can be employed includes jaw crushers, smooth roll crushers, corrugated and tooth-rolled crushers, tumbling mills, cage mills, vibrating mills, jet mills, etc. In general, any type of size reduction equipment can be used with the proviso that the equipment be of a type that generates a minimal amount of heat in the size reduction operation to avoid biuret formation.

One of the advantages of the present invention is that during mechanical compacting and/or size reduction of the compacted masses, if necessary, a certain amount of fines—i.e., particles having a mesh size of 100 or greater—are produced. Unexpectedly, it has been found that these fines have less of a tendency to pack or agglomerate than do the urea crystals, thereby making these fines much more amenable to handling, storing, and shipping. Since in certain uses urea fines are preferred, these by-product fines constitute a commercially attractive product. Additionally, as noted above, the compacted masses can be subjected to size reduction to actually produce such fines, if desired.

Following size reduction, and if desired, classification can be used to obtain a desired particle size. Classifiers that can be used include both gravity and centrifugal types. Thus, for example, screened sieves, centrifugal air classifiers, etc., may be used.

As noted above, urea crystals can be produced that are extremely pure, generally containing greater than 99.0% by weight, most generally greater than 99.5% by weight, urea, and less than 0.25% by weight, most generally less than 0.15% by weight, biuret. Using the method of the present invention, the compacted masses have essentially the same composition as the solid urea crystals. Thus, typically, the compacted masses produced by the method of the present invention contain greater than 99.0% by weight, and most generally greater than 99.5% by weight, urea. Likewise, the biuret content of the compacted masses is less than 0.25% by weight, typically less than 0.15% by weight. It is a feature of the present invention that the compacted masses formed by the method of the present invention have virtually the identical composition as the urea crystals from which they are made. Thus, since urea crystals that contain greater than 99.0% by weight urea and less than 0.1% by weight biuret can be made by processes well known to those skilled in the art, compacted masses having essentially the same composition can be produced according to the present invention. Indeed, it is not uncommon for the urea crystals, and hence the compacted masses, to have urea contents of greater than 99.5% by weight and less than 0.08% by weight biuret. It has also been found that the compacted masses of urea produced by the method of the present invention generally have less than 0.25% by weight water and essentially no formaldehyde or other anti-caking agents.

As noted, the compacted masses of urea produced by the method of the present invention exhibit all the commercially desirable properties of high crush strength, good anti-caking properties, and flowability. As compared to conventional urea prills, the compacted masses of the present invention exhibit somewhat lower dissolution rates in water and other aqueous media. However, as described above, this disadvantage can be readily overcome by size reduction techniques, with or without classification. In any event, the discrete masses of urea produced by mechanical compacting in accordance with the present invention have an extremely low biuret content, making them ideally suitable for any use of urea wherein high biuret content—i.e., greater than 0.25% by weight—cannot be tolerated.

To more fully demonstrate the present invention, the following non-limiting examples are presented.

EXAMPLE 1

Urea crystals containing 99.5% by weight urea, 0.07–0.10% by weight biuret, and 0.70–1.10% by weight water were dried using heated air at a temperature ranging from about 60° C. to about 80° C. and subjected to prilling in a conventional prilling tower. The resulting prills contained 99.5% by weight urea, 0.35–0.38% by weight biuret, and 0.10% by weight water.

EXAMPLE 2

The urea crystals of Example 1 were subjected to pelletizing in a CPM Model 3016-4 pelletizer. The inlet temperature in the pelletizer ranged from 68–79° C., while the outlet temperature ranged from 99–110° C. The pellets had a diameter of 3/16" and a length varying between 1/4" and 1/2". The pellets were found to contain 99.5% by weight urea, 0.07% by weight biuret, and 0.10% by weight water.

It can be seen by comparing the results of Examples 1 and 2 that prilling of very pure urea crystals containing less than 0.10% by weight biuret results in a greater than threefold increase in the biuret content, whereas by using the mechanical compacting method of the present invention, the resulting discrete masses (pellets) show no increase in biuret content.

The foregoing description and examples illustrate selected embodiments of the present invention. In light thereof, variations and modifications will be suggested to one skilled in the art, all of which are in the spirit and purview of this invention.

What is claimed is:

1. A method for producing urea having a low biuret content comprising:
   providing solid crystals of urea having a biuret content of less than 0.25% by weight; and
   forming said solid crystals into discrete masses of urea by mechanical compacting.

2. The method of claim 1 wherein said solid crystals are obtained by separating urea crystals from a mother liquor and drying said separated crystals at a temperature of from 55–95° C.

3. The method of claim 2 wherein said separation is accomplished by centrifugation.

4. The method of claim 2 wherein said drying is conducted by contacting said separated crystals with heated air.

5. The method of claim 1 wherein said mechanical compacting is accomplished by pellitizing.

6. The method of claim 1 wherein said mechanical compacting is accomplished by briquetting.

7. The method of claim 1 wherein said mechanical compacting is accomplished by roll pressing.

8. The method of claim 1 wherein the discrete masses of urea are subjected to size reduction to produce urea particles smaller than the discrete masses.

9. The method of claim 8 wherein said particles are classified to obtain a desired particle size.

10. The method of claim 1 wherein said discrete masses contain less than 0.25% by weight biuret.

11. The method of claim 1 wherein said solid crystals of urea comprise greater than 99.0% by weight urea and less than 0.15% by weight biuret.

12. The method of claim 11 wherein said discrete masses comprise greater than 99.0% by weight urea and less than 0.15% by weight biuret.

13. The method of claim 1 wherein said solid crystals comprise greater than 99.5% by weight urea and less than 0.15% by weight biuret.

14. The method of claim 13 wherein said discrete masses comprise greater than 99.5% by weight urea and less than 0.15% by weight biuret.

* * * * *